United States Patent
Niazi

(10) Patent No.: US 9,469,834 B2
(45) Date of Patent: *Oct. 18, 2016

(54) NON-INVASIVE BIOREACTOR MONITORING

(71) Applicant: Therapeutic Proteins International, LLC, Chicago, IL (US)

(72) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 529 days.

This patent is subject to a terminal disclaimer.

(21) Appl. No.: 14/012,594

(22) Filed: Aug. 28, 2013

(65) Prior Publication Data

US 2013/0344584 A1  Dec. 26, 2013

Related U.S. Application Data

(63) Continuation of application No. 13/279,220, filed on Oct. 21, 2011, now Pat. No. 8,545,759.

(51) Int. Cl.
C12M 1/34 (2006.01)
G01N 21/85 (2006.01)

(52) U.S. Cl.
CPC ............ *C12M 41/00* (2013.01); *C12M 41/26* (2013.01); *C12M 41/32* (2013.01); *C12M 41/34* (2013.01); *C12M 41/36* (2013.01); *G01N 21/8507* (2013.01)

(58) Field of Classification Search
CPC .... C12M 41/26; C12M 41/00; C12M 41/34; C12M 41/36; C12M 41/32; G01N 21/8507

USPC .......... 422/52, 400–405, 82.01–82.09, 68.1, 422/119; 436/34, 149, 150, 164, 172; 435/285.1, 287.1, 287.5, 289.1, 303.1, 435/288.7

See application file for complete search history.

(56) References Cited

U.S. PATENT DOCUMENTS

| | | |
|---|---|---|
| 5,164,796 A | 11/1992 | Di Guiseppi et al. |
| 5,372,936 A | 12/1994 | Fraatz et al. |
| 5,623,095 A | 4/1997 | Beller |
| 5,858,769 A | 1/1999 | DiGuiseppi et al. |
| 6,573,991 B1 | 6/2003 | Debreczeny et al. |
| 6,730,471 B1 | 5/2004 | Katerkamp et al. |
| 7,407,799 B2 | 8/2008 | Balagadde et al. |
| 2003/0092178 A1 | 5/2003 | Yerden |
| 2007/0159920 A1 | 7/2007 | Baumfalk et al. |
| 2007/0292940 A1 | 12/2007 | Roll |
| 2008/0248587 A1 | 10/2008 | Lagwinski et al. |
| 2009/0148931 A1 | 6/2009 | Wilkerson et al. |
| 2010/0035337 A1 | 2/2010 | Bahnemann et al. |
| 2011/0124035 A1 | 5/2011 | Broadley et al. |

OTHER PUBLICATIONS

International Search Report and Written Opinion for PCT/US12/58720, mailed on Dec. 20, 2012.

*Primary Examiner* — Shogo Sasaki
(74) *Attorney, Agent, or Firm* — Therapeutic Proteins International, LLC; Sarfaraz K. Niazi

(57) ABSTRACT

A pair or receptacles capable of housing an emitter probe and a detector probe installed inside a bioreactor to monitor the properties of the nutrient media without contacting the nutrient media.

7 Claims, 2 Drawing Sheets

NON-INVASIVE BIOREACTOR MONITORING

CROSS REFERENCE TO RELATED APPLICATION

This application is a continuation of U.S. patent application Ser. No. 13/279,220 entitled "NONINVASIVE BIOREACTOR MONITORING" filed on Oct. 21, 2011, now U.S. Pat. No. 8,545,759, the contents of which are incorporated herein by reference in its entirety.

BACKGROUND

Bioreactors used for growing cells and organisms need frequent monitoring of the nutrient media to adjust its characteristics to optimize growth. Most commonly it is done by sampling the nutrient media through a port in the bioreactor, which carries the risk of contaminating the bioreactor; also used is the method of routing the nutrient media through a flow cell, which still contains the risk of contamination. More recently, the monitoring has been done by using disposable sensors, which are installed inside a bioreactor and reading their responses from outside the bag; while this method offers a practical choice, it remains less desirable due to its high variability of responses and the high cost of using this method.

There remains an unmet need to create a method for directly monitoring the characteristics of the nutrient media in a bioreactor without removing the nutrient media from the bioreactor to record such parameters as pH, optical density, cell count, dissolved oxygen, dissolved carbon dioxide, glucose concentration and other specific parameters for which a detector is available.

The present invention allows placement of emitter probes of electromagnetic or sound waves inside a bioreactor without contacting the nutrient media and also places a detector of electromagnetic or sound waves inside the bioreactor without contacting the nutrient media. Disposable receptacles receptacle the emitter probe and detector probes are fully transparent to the chosen radiation or wave type employed. The distance between the emitter probe and the detector probe are adjusted by positioning these at different heights when using a V-shaped receptacle or by installing them apart at a pre-determined distance inside a bioreactor. The nutrient media between the transmitter and detector serves as the tested sample.

The angle of probes determines whether the measured radiation is transmitted or diffracted; when facing, the measurement is of transmitted radiation and when placed at an angle such that the path of the line of sight of the probes crosses, measured radiation is diffracted radiation.

The method of present invention involves installing a receptacle inside a disposable bioreactor such that the receptacles for emitter probes and detectors are accessible from outside; the receptacle can also be used in non-disposable bioreactors.

The present invention offers a cost-effective solution to monitoring bioreactors since the expensive emitter probes and detectors are re-used and only the receptacle that houses them is disposed after a single use.

DESCRIPTION OF THE DRAWINGS

FIG. 1(*a*) is the side view of a V-shaped receptacle showing placement of probes; FIG. 1(*b*) is a side view of a V-shaped receptacle showing probes and the path of radiation to measure diffraction; FIG. 1(*c*) is a side view of a V-shaped receptacle showing probes and a straight path of radiation to measure transmitted radiation; FIG. 1(*d*) is a side view of a bioreactor showing a V-shaped receptacle disposed inside the bioreactor showing direct access of the cavity inside the receptacle from the outside of bioreactor.

FIG. 2(*a*) is a side view of two receptacles and probes placed inside the receptacles; FIG. 2(*b*) is an angled view of two receptacles and probes placed inside both receptacles and the paths of radiation.

DETAILS OF THE INVENTION

Optimal operations of a process in a bioreactor require monitoring such parameters as pH, dissolved oxygen, dissolved carbon dioxide, optical density, cell count, glucose concentration and a variety of other parameters specific to the process. The reason for monitoring these parameters is to allow adjustment of the conditions or chemical composition of the nutrient media to optimize the growth profile of cells and organisms in the bioreactor.

Great advances have been made in spectrophotometric technique wherein several parameters of the property of nutrient media can be monitored using visible, ultraviolet and infra red wave lengths of light; the use of ultrasound and microwave along with lasers has further improved the ability of the spectrometers to detect the properties of nutrient media; additionally, improvements in electronic designs, more versatile and miniaturized emitter probes and detectors in the future will make it more convenient and practical to monitor the characteristics of the nutrient media in a bioreactor more effectively and efficiently if it is possible to use these probes non-invasively inside the bioreactor.

The most effective method of monitoring the properties of the nutrient media is to subject its sample to photo or acoustic radiation and from the differences in the emitted radiation and the detected radiation allow assessment of the specific property of nutrient media. There is an unmet need to allow the spectrophotometers and acoustic meters to operate without removing the nutrient media from the bioreactor and without contacting the nutrient media.

This is accomplished in the present invention by installing a V-shaped receptacle made of a material that is transparent to the radiation used; the two arms of the V-shaped receptacle are accessible from the outside to insert emitter probe and detectors. The position of probes determines the distance between them; pushing the probes deep into the receptacle reduces the distance between them. Since the nutrient media monitored resides between the two arms of the receptacle, monitoring the nutrient media of higher concentration will require reducing the length of the passage of light by pushing the probes upwards toward the junction of the two arms of the V-shaped receptacle.

In a more general use of the invention, the probes are inserted in independent receptacles that are attached to the bottom of a bioreactor.

The emitter and emitter probes can be rotated to an angle such that the emitted radiation is detected from the dispersion or diffraction of the radiation by the detector. This will be analogous to measuring turbidity rather than transmission, which is measured when the two probes face each other.

Figure 1:
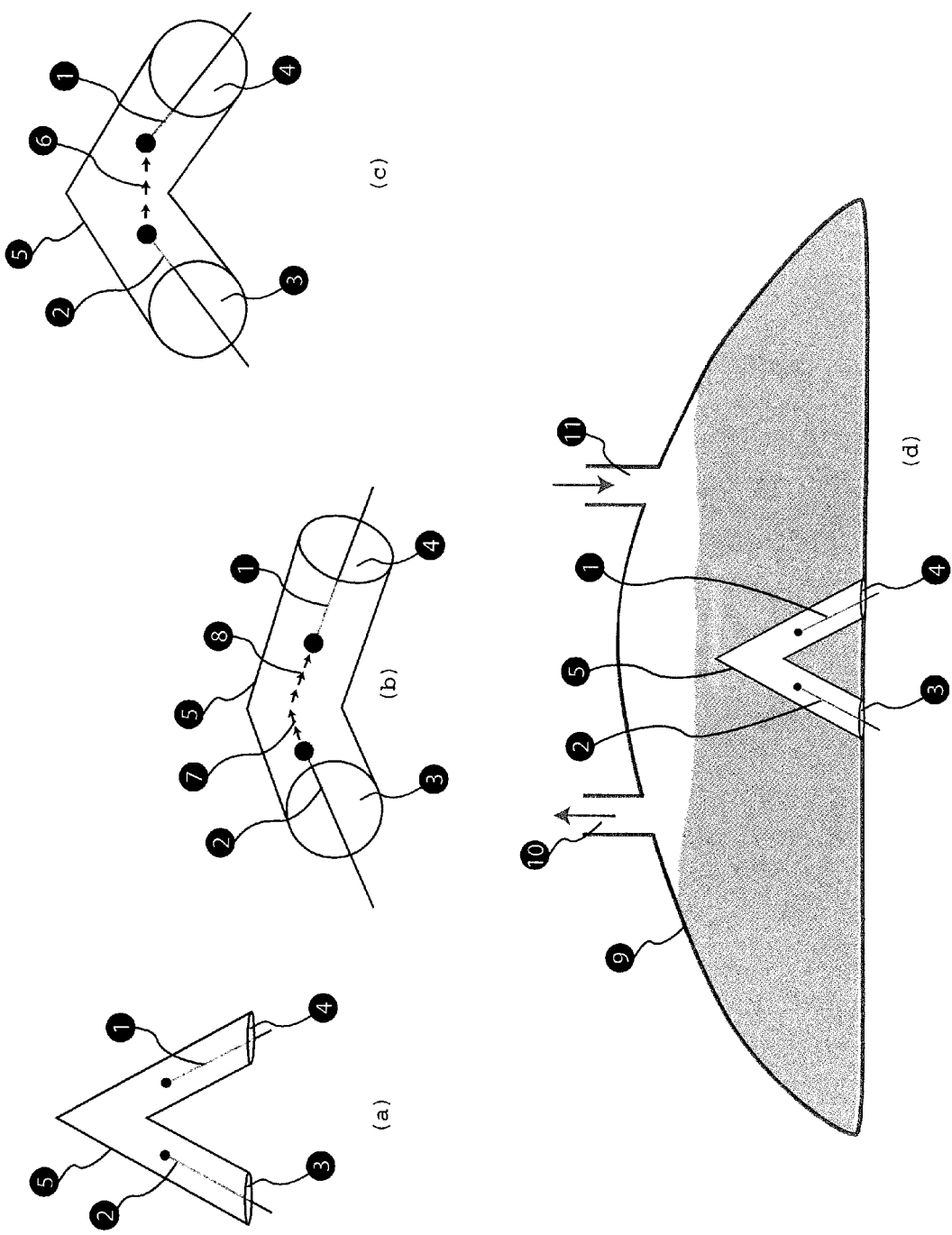
FIG. 1 shows many view of a V-shaped receptacle.

A first preferred embodiment is shown in FIG. 1, wherein a V-shaped receptacle 5 has an inner cavity capable of holding probes 1 and 2 and openings 3 and 4 to insert the probes. The path of radiation emitted 7 at an angle to the detector probe path 8 shows how diffracted radiation is detected. When the probes are facing they create a straight path 6 that allows measurement of transmitted radiation. The receptacle 5 is installed inside a bioreactor 9 preferably attached to the bottom surface of the bioreactor such that the openings 3 and 4 allow fluid communication of the cavity inside the receptacle 5 from the outside of the bioreactor, which may additionally container an inlet 11 and an outlet 10 and nutrient media totally submerging the receptacle 5.

Figure 2:
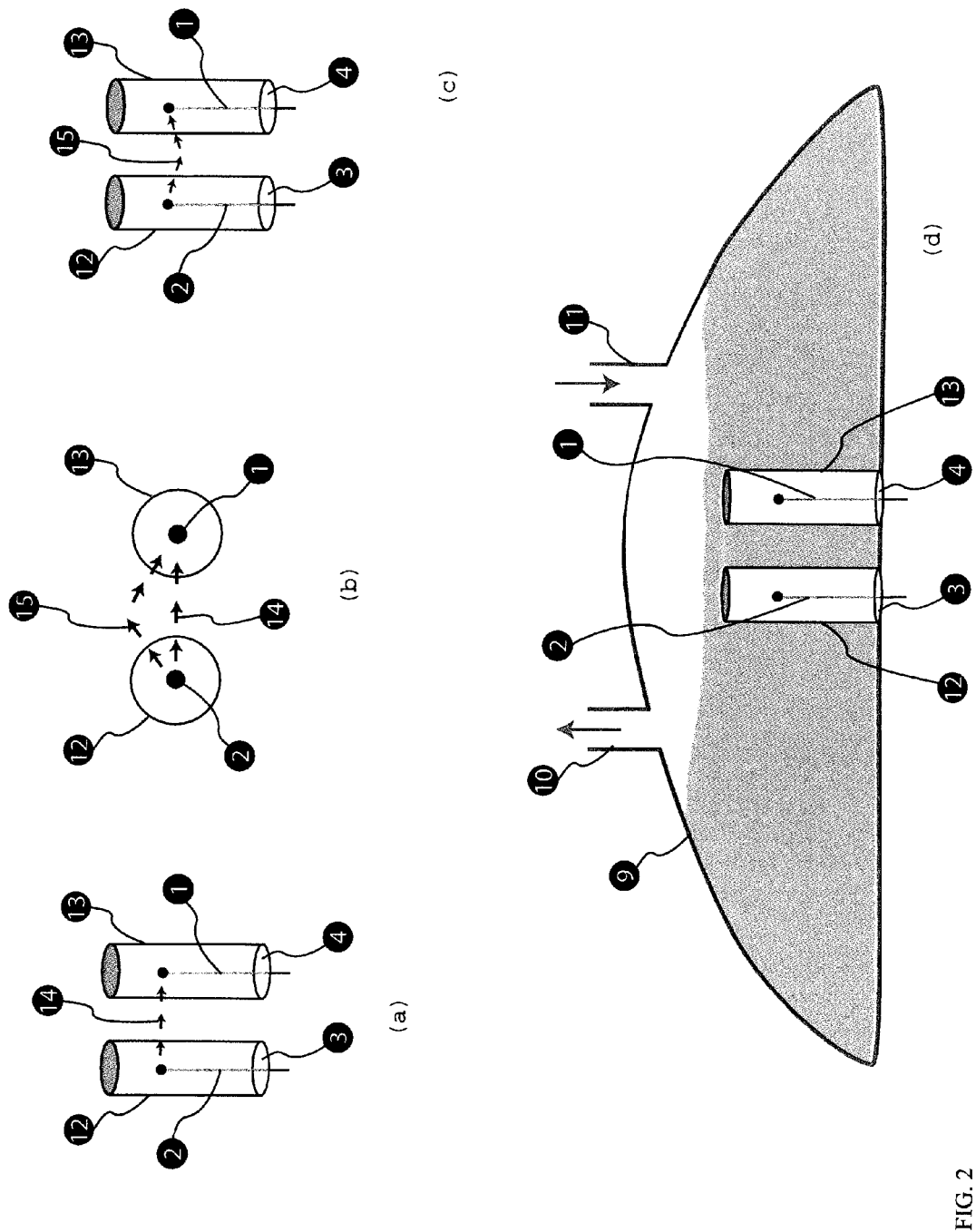
FIG. 2 shows many views of two receptacles installed at a fixed distance from each other.

FIG. 2 is another preferred embodiment wherein instead one V-shaped receptacle as shown in FIG. 1, there are two independent receptacles, one receptacle 2 to hold the emitter probe and one receptacle 13 to hold the receptor; the path of transmission 14 across the two receptacles and when the path of radiation is placed at an angle 15, it used to determine diffraction. When installed in container 9, the devices are attached to the bottom of container 9 that may have an inlet port 11 and an exhaust 10.

The present invention thus offers a practical solution to monitoring the nutrient media non-invasively while using traditional methods of recording the properties of the nutrient media.

The present invention will prove to be continuously beneficial as new probes are developed enhancing the utility of the present invention to monitor the nutrient media inside a bioreactor without affecting its sterility or without breaching the integrity of the bioreactor and without removing a sample from the bioreactor.

The emitter probes and detectors used in the present invention are non-disposable and thus the cost of operations is reduced substantially while affording the highest sensitivity and repeatability of the monitoring operations.

The ability to monitor a variable depth of nutrient media is of great advantage to monitor the nutrient media over a wide range of the concentration of the entities monitored; this is analogous to diluting samples to study their properties. The distance between the probes represents the depth of liquid monitored and this is changed by moving the probes up or down toward the apex of the V-shaped receptacle.

The present invention also provides a solution to monitoring the nutrient media by installing a disposable receptacle inside a bioreactor—a receptacle that is accessible from the outside of the bioreactor to insert emitter probes and detectors inside the bioreactor without touching the nutrient media. The material of construction of the receptacle is same as it is used in spectrophotometers, wherein the walls of the receptacle are transparent to specific electromagnetic or sound waves; these receptacle elements are inexpensive to construct and eliminate the need for using a disposable emitter probe or detector.

The present invention also offers a novel solution combining the use of disposable patches or probes installed inside a bioreactor wherein these probes emit fluorescence upon reacting with the content of the nutrient media. The fluorescence is then detected by the detector housed in the receptacle to allow for a high degree of accuracy in measurements. Using the present invention, these probes can be monitored more closely and more accurately by bringing the detector element closer to these patches inside the bioreactor. In this instance, the patches can be attached to the receptacle portions that are exposed to the nutrient media and the detector may include a source of light as well to excite the fluorescent probe.

The present invention can be used to measure various parameters non-invasively inside a bioreactor; these parameters include but not limited to temperature, pH, optical density, dissolved oxygen, dissolved carbon dioxide, glucose concentration and other chemical entities.

While optical density is a good indicator of the growth of bacterial culture, mammalian cell culture requires counting the cells in a specific volume. Since a small volume of liquid media is present between the receptacles holding the emitter probe and the emitter probe, installing an optical element such as a microscope lens or a camera pointed towards the liquid between the two receptacles to count the cells remotely. It is noteworthy that the material used for the construction of receptacle is transparent to light without producing any distortion and thus allowing the microscopy work more reliable. Alternately, a camera can record the images of cells and the photograph then read to calculate the density of cells.

The use of acoustic waves, both sound and ultrasound, in analytical methods is a fast developing science; materials transparent to sound and ultrasound waves are widely available and receptacles can be made out of these materials to allow probing using sound and ultrasound waves as well in the present invention.

What is claimed is:

1. A device for non-invasive, non-contact monitoring of a nutrient media in a bioreactor comprised of a container with a top surface, a bottom surface, and an inner volume capable of holding the nutrient media, the device comprising:
    at least one pair of receptacles suitable for housing probes, the receptacles configured for hermetically sealing the probes from the nutrient media; and each comprising one open end in fluid communication with the outside of the bioreactor via the bottom surface and one sealed end;
    an emitter probe capable of producing an electromagnetic or acoustic signal disposed in a first receptacle of the at least one pair of receptacles;
    a detector probe capable of detecting an electromagnetic or acoustic signal disposed in a second receptacle of the at least one pair of receptacles;
    wherein the distance between the first receptacle and the second receptacle can be varied by adjusting the first receptacle and the second receptacle up and down, or sideways, wherein the distance between the receptacles represents the depth of the nutrient media monitored; and
    an electronic means for converting a signal received from the detector probe into physical and chemical properties of the nutrient media.

2. The device of claim 1, wherein the electromagnetic signal comprises long wave, radio wave, microwave, thermal infrared, infrared, visible, fluorescent, ultraviolet, x-rays and gamma ray signal.

3. The device of claim 1, wherein the acoustic signal comprises sound wave and ultrasound wave signal.

4. The device of claim 1, wherein the device is used to monitor temperature, pH, optical density, cell count, dissolved oxygen, dissolved carbon dioxide, and glucose concentration in the nutrient media either continuously or intermittently.

5. The device of claim 1, wherein the receptacles are made of plastic, glass or fused quartz.

6. The device of claim 1, wherein the receptacles are round, square or rectangular tubes.

7. The device of claim 1, wherein the sealed ends of receptacles are joined.

* * * * *